United States Patent [19]
Lidgren et al.

[11] Patent Number: 5,501,520
[45] Date of Patent: Mar. 26, 1996

[54] DEVICE FOR PRODUCING REDUCED POROSITY BONE CEMENT

[75] Inventors: Lars Å A. Lidgren; Lars G. Dahl, both of Lund, Sweden

[73] Assignee: MIT AB, Sjobo, Sweden

[21] Appl. No.: 233,697

[22] Filed: Apr. 26, 1994

Related U.S. Application Data

[62] Division of Ser. No. 13,074, Feb. 3, 1993, Pat. No. 5,328,262.

[30] Foreign Application Priority Data

Feb. 7, 1992 [SE] Sweden ............................. 9200360-7

[51] Int. Cl.$^6$ .................................................. B01F 13/06
[52] U.S. Cl. ............................................ 366/139; 366/256
[58] Field of Search ................................. 366/129, 130, 366/139, 189, 191, 194, 242, 255–257, 332, 333, 348, 602; 206/219, 221; 222/152, 229, 325–327, 386, 567–568

[56] References Cited

U.S. PATENT DOCUMENTS

| | | |
|---|---|---|
| 2,453,914 | 11/1948 | Hollenback . |
| 2,696,022 | 12/1954 | Steinbock et al. . |
| 2,973,187 | 2/1961 | Wehmer . |
| 3,131,912 | 5/1964 | Steinbock, Jr. . |
| 3,358,971 | 12/1967 | Steinbock, Jr. . |
| 3,366,369 | 1/1968 | Ravasi . |
| 3,559,961 | 2/1971 | Bergendal . |
| 3,640,510 | 2/1972 | Lea . |
| 4,185,072 | 1/1980 | Puderbaugh et al. ............... 366/139 X |
| 4,277,184 | 7/1981 | Solomon ............................. 366/139 X |
| 4,463,875 | 8/1984 | Tepic .................................... 206/219 X |
| 4,469,153 | 9/1984 | Morrisette ........................... 366/256 X |
| 4,721,390 | 1/1988 | Lidgren .................................... 366/139 |
| 4,758,096 | 7/1988 | Gunnarsson ............................. 366/139 |
| 4,787,751 | 11/1988 | Bakels ................................ 366/139 X |
| 4,799,801 | 1/1989 | Bruning .................................... 366/255 |
| 4,889,432 | 12/1989 | Patterson ........................... 366/177 X |
| 4,961,647 | 10/1990 | Coutts et al. ............................ 366/139 |
| 4,973,168 | 11/1990 | Chan ........................................ 366/139 |
| 5,121,990 | 6/1992 | Guiet et al. ............................. 366/139 |
| 5,252,301 | 10/1993 | Nilson et al. ........................ 366/255 X |

FOREIGN PATENT DOCUMENTS 462315  6/1990  Sweden .

Primary Examiner—Charles E. Cooley
Attorney, Agent, or Firm—Foley & Lardner

[57] ABSTRACT

A mixing device for producing reduced porosity bone cement. The device having a movable member (6), preferably a movable piston, which is adapted to press out or discharge bone cement (2) from the mixing device (1). The piston is fixedly mounted in the mixing device. The piston maintains its position when bone cement (2) is mixed in a mixing space in the mixing device. The mixing device is under a vacuum during mixing. After mixing, the piston is released such that it can be drawn into the mixing device (1) toward a discharge opening (13) by a vacuum prevailing in the mixing device (1). The moving piston is used for collecting clumps of bone cement (2) in the mixing device (1) adjacent to the discharge opening (13). By collecting the clumps of bone cement by the moving piston (6) under a vacuum, the porosity of the bone cement (2) is reduced.

9 Claims, 7 Drawing Sheets

5,501,520

DEVICE FOR PRODUCING REDUCED POROSITY BONE CEMENT

This application is a division, of application Ser. No. 08/013,074, filed Feb. 3, 1993, now U.S. Pat. No. 5,328,262.

FIELD OF THE INVENTION

The present invention relates to a method for producing bone cement by mixing components forming part thereof, whereby mixing occurs in vacuum in a mixing device and whereby ready-mixed bone cement is collected in the mixing device before it is ejected therefrom. The invention also relates to a device for carrying out said method.

RELATED ART

In order to impart advantageous properties to the bone cement, the components required for the manufacture are mixed in vacuum. Such methods and devices for carrying out said methods are known from e.g. U.S. Pat. Nos. 4,721,390 and 4,758,096. By carrying out the mixture of the components in vacuum in accordance with these specifications, the porosity in the bone cement may be reduced.

When the bone cement is mixed, it is often adhering "in clumps" to the various wall portions of the mixing space and/or to the mixing means situated in the mixing space. The higher the viscosity of the bone cement, the higher the tendency to adhere in clumps in this way.

Before the bone cement is removed from the mixing space, it is normally collected until all bone cement is collected at the front in said mixing space. During this collection, pores are formed in the bone cement and this is disadvantageous because the bone cement thereby may loose the properties aimed at by producing said bone cement in vacuum.

SUMMARY OF THE INVENTION

The object of the present invention is to eliminate said problem and this is arrived at according to the invention by means of a method the characterizing features of which include the mixing of bone cement components under vacuum in a mixing space of a mixing device, whereby clumps of bone cement are caused to adhere to an inner wall surface of the mixing space, and collecting the clumps of bone cement close to a discharge opening which is adapted to discharge the bone cement from the mixing space. The collecting step further includes the steps of exposing the bone cement in the mixing space to a vacuum and moving a piston through the mixing space toward the discharge opening to collect the bone cement near the opening, thereby providing vacuum in those pores in the bone cement which are formed during collection of the bone cement clumps. In this manner, the pores formed in the bone cement are reduced in size when the bone cement is ultimately subjected to atmospheric pressure after collection.

By reducing the volume of porosity of the bone cement obtained during collection thereof, it is possible for the bone cement to maintain the properties acquired during the production thereof in vacuum.

By carrying out the collection of the bone cement by releasing a movable member—preferably a piston by means of which the bone cement is fed out of the mixing space— such that said movable member because of vacuum in the mixing space can be sucked into said space, one and same member can be used for collection in vacuum as well as ejecting thereafter.

BRIEF DESCRIPTION OF THE DRAWINGS

The invention will be further described below with reference to the accompanying drawings, wherein.

DETAILED DESCRIPTION OF THE PREFERRED EMBODIMENTS

Figure 1:
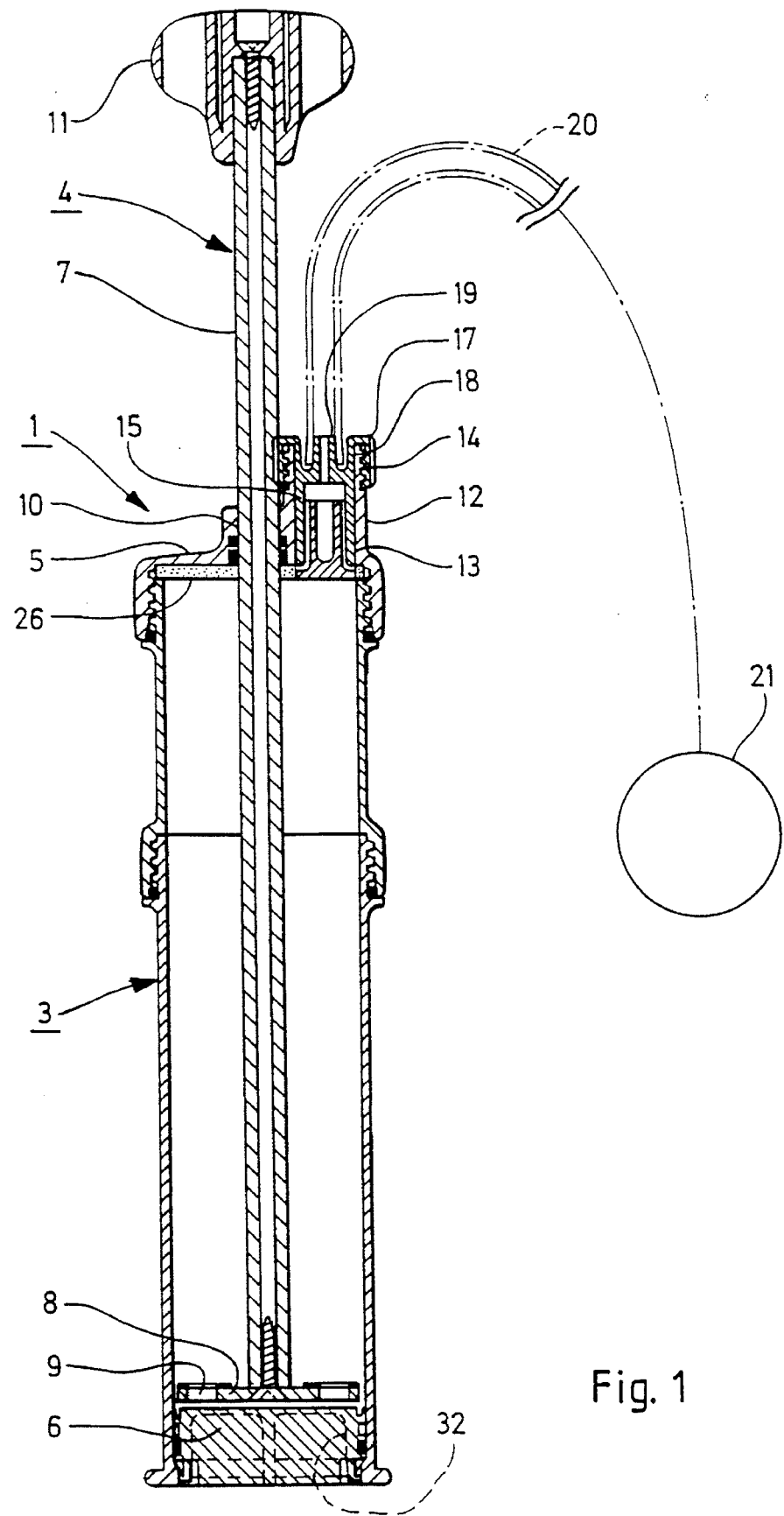
FIG. 1 is a section of a device for mixing and applying bone cement, which device is constructed according to the invention and usable for carrying out the method according to the invention.
Figure 2:
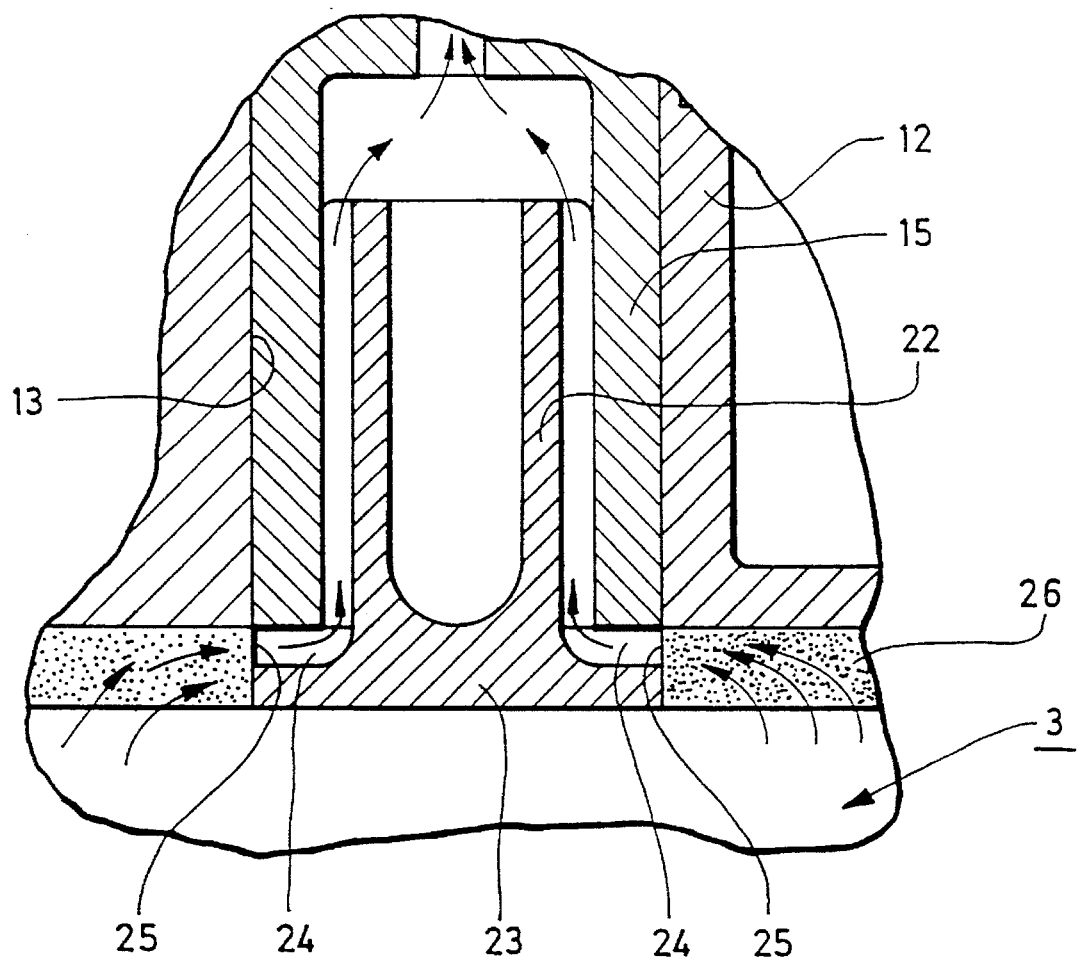
FIG. 2 is a section of a front portion of the device according to FIG. 1.

The mixing device 1 illustrated in the drawings is adapted to permit mixing of various components for producing bone cement 2. For this purpose, the mixing device 1 comprises a mixing cylinder 3 with a mixing means 4. At the front, the mixing cylinder 3 is sealable by means of a cap 5 and said mixing cylinder 3 further includes a movable member 6, preferably a piston, which can be fixed at the rear in said cylinder and released therefrom for movement further into the cylinder.

The mixing means 4 preferably consists of an operating rod 7 the part of which located inside the mixing cylinder 3 is provided with a mixing plate 8 with a number of through-flow holes 9. The operating rod 7 protrudes out of the mixing cylinder 3 through an aperture 10 in the cap 5 and the part thereof situated outside said mixing cylinder 3 is provided with a handle 11.

The cap 5 preferably comprises a protruding tube section 12 which is adapted to define the discharge opening 13 for bone cement and the outer end of which is provided with external threads 14. A plug 15 can be screwed on these threads 14 for use when producing and collecting the bone cement 2, and a discharge pipe 16 for facilitating the application of the bone cement 2 at the desired location during discharge thereof from the mixing cylinder 3.

To permit screwing of the plug 15 on the threads 14 of the tube section 12, the outer end of said plug is provided with a rearwardly directed flange 17 with internal threads 18. The outer end of the plug 15 further comprises a connecting-pipe section 19 to which a hose 20 to a vacuum source 21 can be connected.

The plug 15 further comprises an inner member 22 with a bottom portion 23 which is adapted to prevent bone cement 2 from forcing its way out of the mixing cylinder 3 during the production and collection thereof. The bottom portion 23 has or defines radially directed gas passage branches 24, the inlets 25 of which lie within a filter material disk 26 of such filter material that permits penetration of gas but not bone cement 2. The filter material disk 26 is placed between an end edge of the mixing container 3 and the cap 5 and it engages the bottom portion 23 of the inner member 22 such that only gas but not bone cement 2 can pass into the inlets 25 of the passage branches 24. The passage branches 24 communicate with the connecting-pipe section 19 of the plug 15, whereby gas, by means of the vacuum source 21, can be sucked out of the mixing cylinder 3 through the filter material disk 26.

When bone cement 2 is ready-mixed and collected in the mixing cylinder 3, the plug 15 is unscrewed, whereby the discharge opening 13 in the protruding tube section 12 is exposed. Thereafter, the discharge pipe 16 is screwed on the threads 14 of the protruding tube section 12, which is made possible by means of internal threads 27 on said discharge pipe 16.

Figure 4:
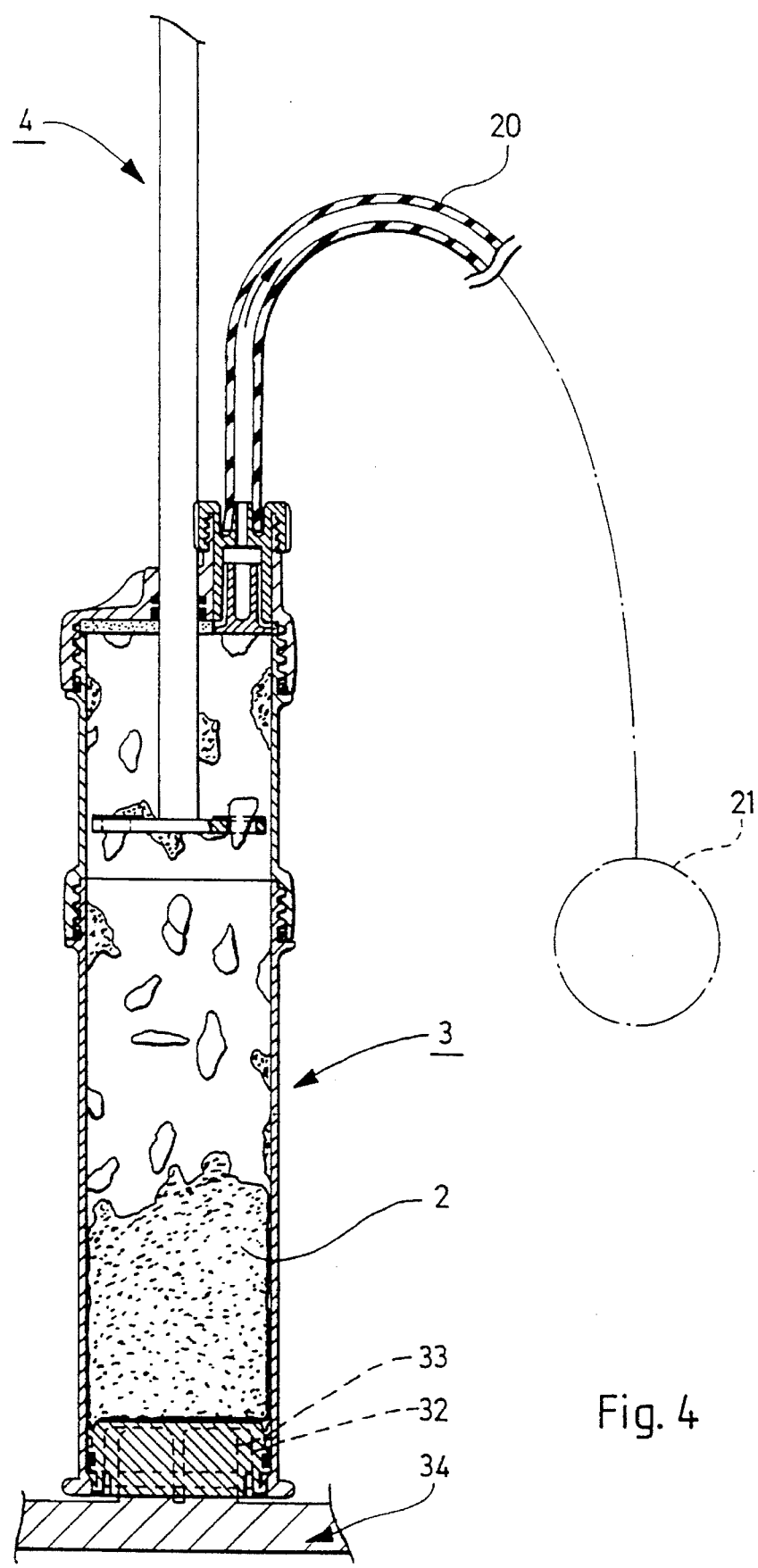
FIG. 4 is a schematic view of the device of FIG. 1 after mixing the components such that bone cement is produced.

The movable piston 6 can be fixed at the rear in the mixing cylinder 3 such that it does not move when mixing of bone cement 2 occurs in said mixing cylinder 3. The piston 6 is also releasable and designed such that it can be brought to move farther into the mixing cylinder 3 when there is a vacuum therein for collecting the ready-mixed bone cement 2 at the front in the mixing cylinder 3 closest to the discharge opening 13. To enable this fixing and release of the piston 6, the mixing cylinder 3 has at the rear preferably at least one oppositely directed gripping portion 28, which e.g. can have the shape of a flange which extends only along a portion of the inner periphery of the mixing cylinder 3. The piston 6 on the other hand, has at least one corresponding gripping portion 30 shaped preferably as an outwardly directed lip which can protrude behind the gripping portion 28 of the mixing cylinder 3. The lip preferably defines a groove with the outer side of the piston into which the gripping portion 28 of the mixing cylinder 3 can extend, and said lip is preferably also shaped such that it extends only along a limited portion of the outer periphery of the piston 6. By means of this gripping structure, the piston 6 can be kept fixed to the rear portions of the mixing cylinder 3 and it can be released by rotation relative to the mixing device or vice versa until the gripping portions 28, 30 are disengaged (see position of the gripping portion 28 of the mixing cylinder 3 indicated with dashed and dotted lines in FIG. 4).

To enable release of the piston 6 by simple means and in a simple manner, said piston 6 may have gripping surfaces 32, e.g. one or more recesses in the outer side of the piston 6, which can be brought in engagement with corresponding gripping surfaces 33, e.g. one or more upwardly directed pins, on a separate member 34, located on a base. This separate member 34 can e.g. be a trough which can be placed on the operating table. By positioning the mixing cylinder 3 on the separate member 34 such that the gripping surfaces 32 of the piston 6 and the gripping surfaces 33 on said separate member 34 cooperate with each other, the piston 6 can be released by rotating the mixing cylinder 3 relative to the separate member 34, since the gripping surfaces 33 of said separate member 34 prevent the piston 6 from rotating with the mixing cylinder 3.

Figure 3:
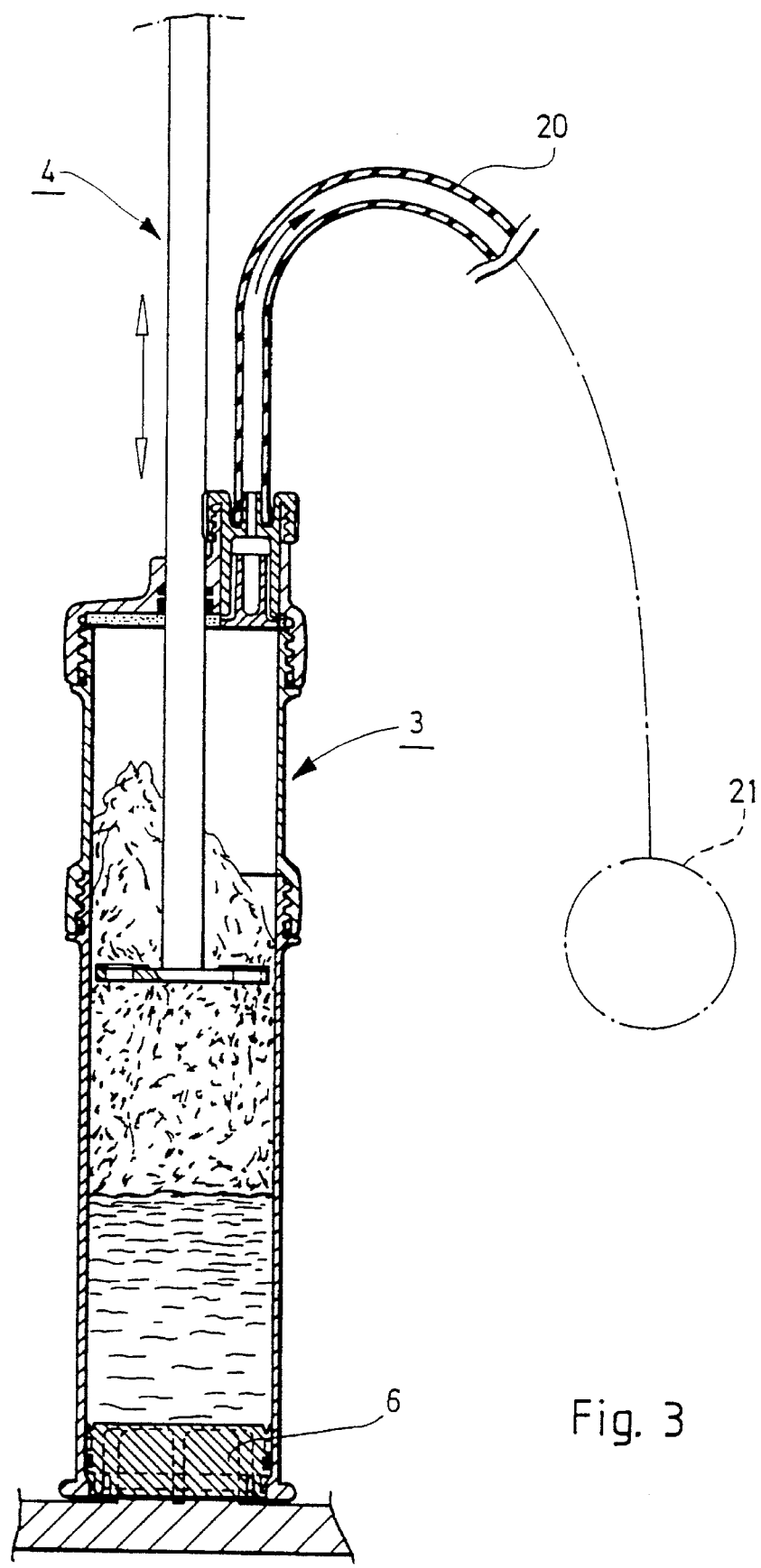
FIG. 3 is a schematic view of the device of FIG. 1 filled with components for producing bone cement in vacuum.

For producing and collecting bone cement 2 of the present type, an appropriate amount and type of components are filled into the mixing cylinder 3 (see FIG. 3). Thereafter, the mixing cylinder 3 is connected to the vacuum source 21 until a predetermined vacuum is generated in said cylinder. Mixing of the components occurs by moving the operating rod 7 up and down in the mixing cylinder 3, whereby the bone cement 2 passes through the holes 10 in the mixing plate 8. This procedure is continued until the components are mixed sufficiently for producing bone cement 2 having predetermined properties.

When the mixing step is concluded, the bone cement 2 is not gathered in the front or fore portions of the mixing cylinder 3. Instead, it is spread in different portions of the mixing cylinder 3 and it can adhere in clumps to the inner surfaces of the mixing cylinder 3, to the mixing plate 8 and eventually also to the operating rod 7 (see FIG. 4) particularly if the viscosity of the bone cement 2 is high. Collection of the bone cement 2 occurs in vacuum in order to generate a vacuum in the pores formed in the bone cement 2 during collection or gathering. Hereby, the volume of porosity in the bone cement 2 is reduced when subjected to atmospheric pressure after gathering, e.g. when the vacuum source is disconnected from the mixing cylinder 3 such that air may flow into said cylinder. Since there is a vacuum in the pores formed during collection or gathering, the volume of porosity in the bone cement 2 is reduced e.g. by the disappearance of smaller pores and a reduction in volume of other pores.

The bone cement 2 can be collected in a vacuum which is maintained after the mixture of the bone cement 2 is ready. Hereby, it is possible during collection or gathering either to maintain the same vacuum as during mixing or alternatively increase or decrease the vacuum present during mixing.

The bone cement 2 can be collected or gathered in at least 40% vacuum and preferably in 80–95% vacuum.

Figure 5:
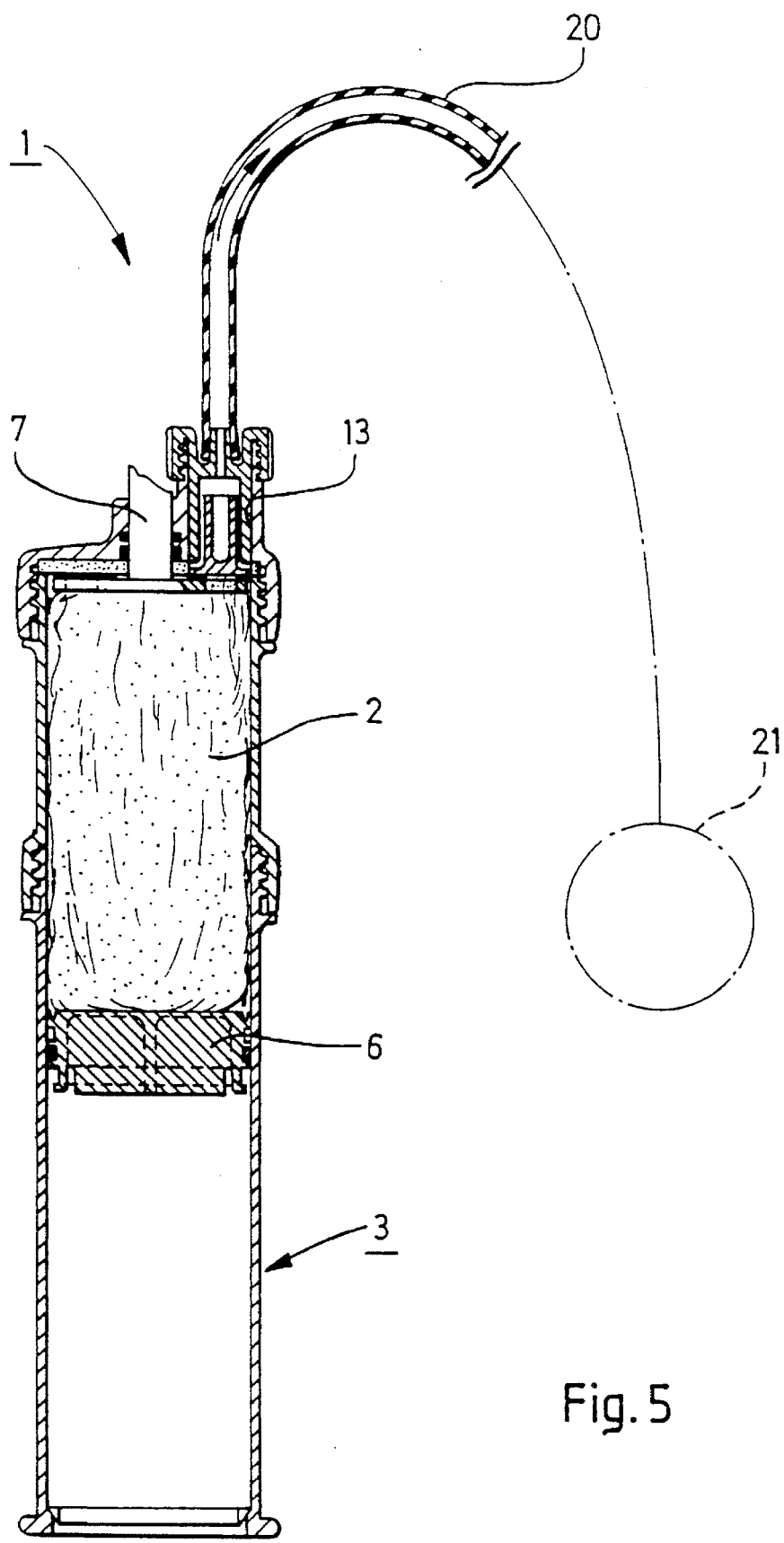
FIG. 5 is a schematic view of the device of FIG. 1 during collection of the bone cement produced.

The collection of bone cement 2 is carried out preferably by means of the piston 6 which after release (see FIG. 5) is sucked into the mixing cylinder 3 while there is a vacuum therein, whereby bone cement 2 is collected at the front in the mixing cylinder.

Gas but not bone cement 2 can pass through the filter material disk 26 to the vacuum source 21 during collection.

Figure 6:
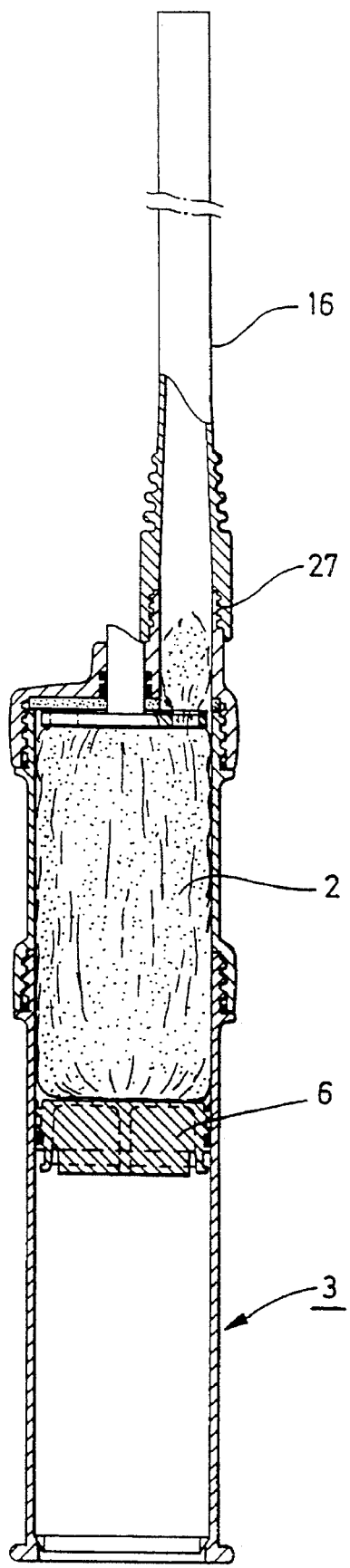
FIG. 6 is a schematic view of the device of FIG. 1 after collecting the bone cement and application of a discharge pipe for discharging or ejecting said bone cement.
Figure 7:
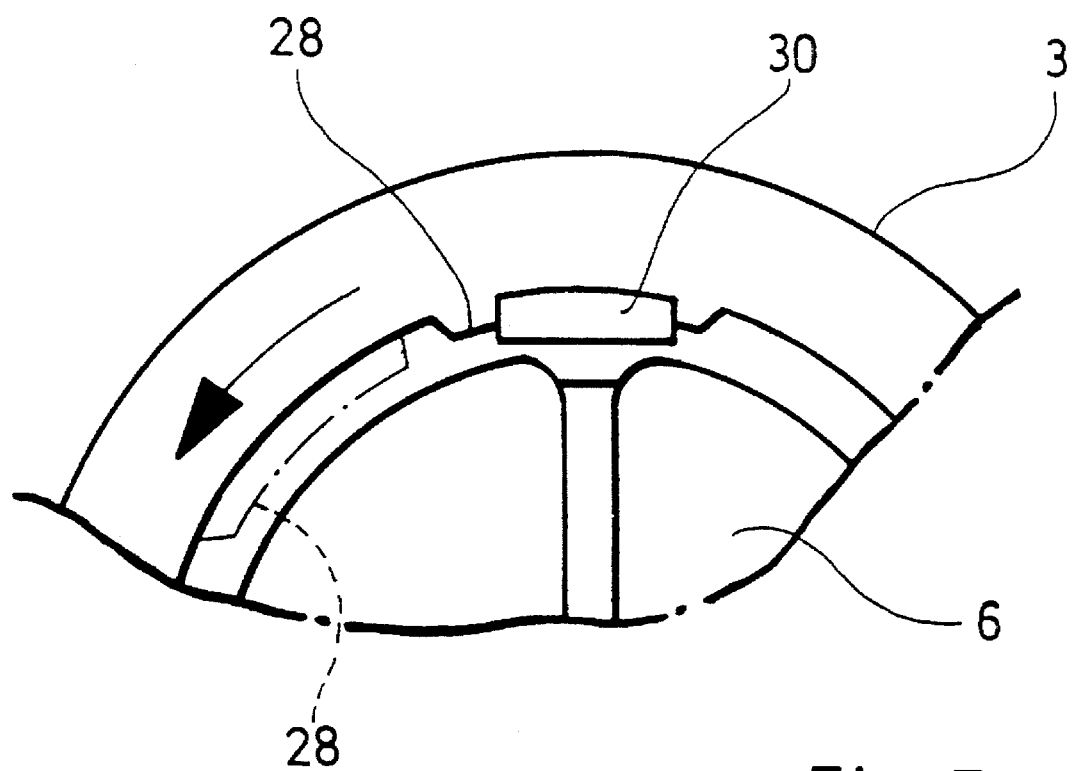
FIG. 7 schematically illustrates a portion of a plan view over a rear portion of the device according to FIG. 1.

After collection of the bone cement 2, the hose 20 is disconnected, the operating rod 7 (which thereby is situated in its upper end position) is broken and the plug 15 removed, whereafter the discharge pipe 16 is connected to the mixing cylinder 3 (see FIG. 6). The mixing device 1 is now ready for use at an operation for application of the finished and collected bone cement 2. The discharge of the bone cement 2 from the mixing cylinder 3 through the discharge opening 13 and discharge pipe 16 is made possible preferably by placing said mixing cylinder 3 in a so called outfeed or discharge pistol (not shown), which is designed such that it can affect the piston 6 in forward direction, whereby said piston 6 is pressing or forcing the bone cement 2 out of the mixing cylinder 3.

By carrying out the mixing of the components as well as the collection or gathering of the finished bone cement 2 in vacuum, a good quality bone cement with insignificant porosity is obtained, which is advantageous for e.g. the tensile or physical properties of the bone cement.

The invention is not limited to the device and method described above. As an alternative, the piston 6 can e.g. be fixed at and releasable from the mixing cylinder 3 in other ways than by means of the gripping portions described, the piston can be designed as another type of movable member and the entire mixing device need not necessarily be a syringe or sprayer.

We claim:

1. A mixing device for producing reduced porosity bone cement, comprising:

a mixing cylinder (3) having a mixing space, the mixing space having wall surfaces to which clumps of bone cement adhere during mixing of components of the bone cement;

means (4) for mixing the components in the mixing space, a front member (5) provided at a front end of the mixing cylinder, the front member (5) having a discharge opening (13) for discharging bone cement from the mixing space, a movable piston (6) fixably mounted at a rear end of the mixing cylinder, the movable piston being releasable from the rear end of the mixing cylinder and movable in the mixing space toward the discharge opening (13) for collecting the clumps of bone cement adjacent the discharge opening, and for discharging bone cement (2) through the discharge opening (13); and a vacuum source (21) connected to the mixing device, generating a vacuum in the mixing space during mixing of the components;

wherein, when the movable piston (6) is released from the rear end of the mixing cylinder and moved in the mixing space for collecting the clumps of bone cement adjacent to the discharge opening (13) such that the vacuum generated in the mixing space by the vacuum source generates a vacuum in pores formed in the bone cement (2) during the collecting of the clumps of bone cement, whereby the size of the pores is reduced when the bone cement (2), after collecting, is exposed to atmospheric pressure; and wherein the vacuum source (21) is connected to the front member (5).

2. A mixing device according to claim 1, wherein the movable piston (6) is moved in the mixing space toward the discharge opening (13) by the vacuum generated by the vacuum source (21).

3. A mixing device according to claim 1, wherein the movable piston (6) comprises at least one gripping portion (30) and the mixing cylinder comprises at least one corresponding gripping portion (28), the gripping portions (28, 30) of the movable piston (6) and the mixing cylinder are engaged with each other for fixing the movable piston (6) to the mixing cylinder, and the gripping portions (28, 30) are disengaged from each other by at least one of: rotating the movable piston (6) relative to the mixing cylinder and rotating the mixing cylinder relative to the movable piston (6).

4. A mixing device according to claim 3, wherein the gripping portions (28, 30) are disengaged from each other by rotating the mixing cylinder relative to the movable piston (6) after the movable piston (6) is placed into engagement with a separate member (34), the separate member prevents the movable piston (6) from rotating when the mixing cylinder is rotated relative to the separate member (34).

5. A mixing device according to claim 1, wherein the front member (5) is a cap adapted to seal the mixing space at the front end of the mixing cylinder, and an aperture (10) for the mixing means (4) is provided in the cap; the discharge opening has a connecting-pipe section (19); and a hose (20) extending from the vacuum source (21) is connected to the connecting-pipe section (19).

6. A mixing device according to claim 5, wherein the connecting-pipe section (19) forms a part of a plug (15) which is located in a tube section (12) provided on the cap.

7. A mixing device according to claim 6, wherein the tube section (12) is provided with external threads (14), and the plug (15) has a flange (17) with internal threads (18) for engagement with the external threads (14).

8. A mixing device according to claim 1, wherein a discharge pipe (16) for discharging bone cement from the mixing space is provided on a tube section (12) formed on the front member (5).

9. A mixing device according to claim 8, wherein the discharge pipe (16) is provided with internal threads (27) for engagement with external threads (14) provided on the tube section (12).

* * * * *